United States Patent [19]

Shigeta et al.

[11] Patent Number: 4,748,983
[45] Date of Patent: Jun. 7, 1988

[54] X-RAY TRANSMISSIVE ELECTRODE FOR A LIVING BODY

[75] Inventors: Masatomo Shigeta; Hikonori Abe; Shinichi Nishiyama, all of Iwaki, Japan

[73] Assignee: Kureha Kagaku Kogyo Kabushiki Kaisha, Tokyo, Japan

[21] Appl. No.: 898,386

[22] Filed: Aug. 20, 1986

[30] Foreign Application Priority Data

Aug. 27, 1985 [JP] Japan ................................ 60-187595
Nov. 25, 1985 [JP] Japan ................................ 60-264655

[51] Int. Cl.⁴ .......................... A61B 5/04; A61N 1/04
[52] U.S. Cl. .................................. 128/639; 128/798; 128/803
[58] Field of Search ........................... 128/639–641, 128/643, 644, 783, 784–786, 798, 802, 803, 419 P, 419 D

[56] References Cited

U.S. PATENT DOCUMENTS

| 3,722,005 | 3/1973 | Cowland | 128/642 X |
| 4,079,731 | 3/1978 | Danby | 128/641 |
| 4,102,331 | 7/1978 | Grayzel et al. | 128/640 |
| 4,198,991 | 4/1980 | Harris | 128/784 |
| 4,248,237 | 2/1981 | Kenny | 128/419 P |
| 4,417,581 | 11/1983 | Dawson | 128/639 |

FOREIGN PATENT DOCUMENTS

| 1388870 | 10/1971 | Australia | 128/798 |
| 122258 | 2/1972 | Denmark | 128/641 |
| 6940435 | 10/1969 | Fed. Rep. of Germany . | |
| 2830219 | 1/1980 | Fed. Rep. of Germany . | |
| 2842318 | 4/1980 | Fed. Rep. of Germany . | |
| 8320192 | 4/1984 | Fed. Rep. of Germany . | |
| 523697 | 10/1976 | U.S.S.R. | 128/639 |

Primary Examiner—Lee S. Cohen
Attorney, Agent, or Firm—Nixon & Vanderhye

[57] ABSTRACT

Disclosed herein is an electrode for a living body, which is used in a defibrillator and the like without hindering X-ray inspection, the main part of the electrode (hereinafter referred to as "the electrode substrate") comprising a porous material composed of granular or fibrous carbon, or a flexible and porous material composed of fibrous carbon, the electrode being made to be transparent to X-ray.

11 Claims, 4 Drawing Sheets

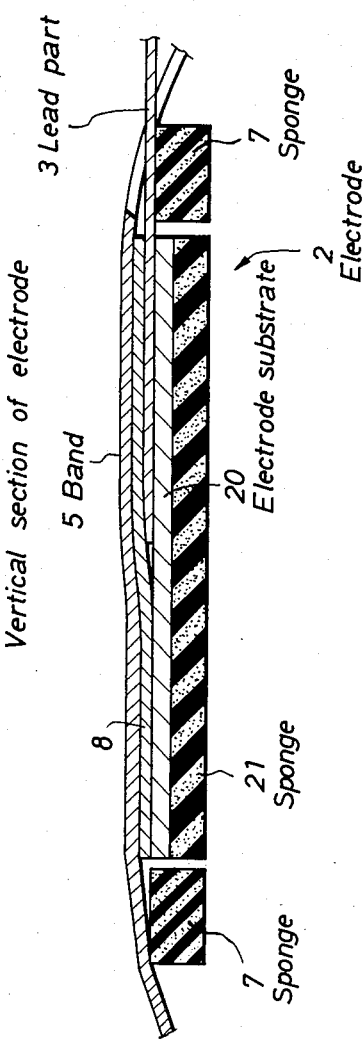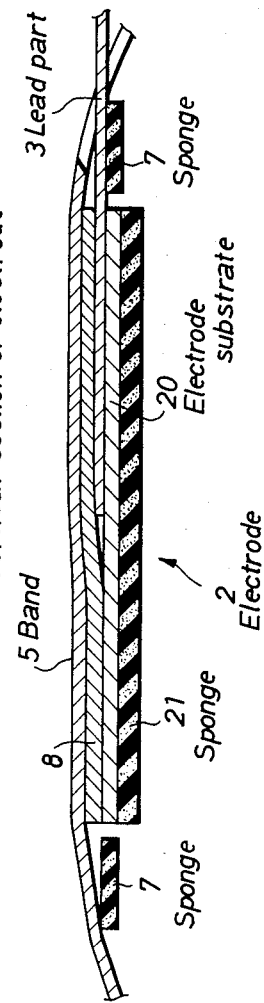

Side view of defibrillator in use

Plane figure of defibrillator in use

Electrode substrate and lead part

Electrode substrate and lead part

Another example of electrode

Flexible sheet

X-RAY TRANSMISSIVE ELECTRODE FOR A LIVING BODY

BACKGROUND OF THE INVENTION

The present invention relates to an electrode for a living body, which is suitably used as the electrode of a defibrillator, an electrocardiograph and the like.

Hitherto, in the case of carrying out the catheter-inspection of the heart, a catheter is inserted into a blood vessel of the patient and after introducing a contrast media into the heart via the blood vessel, X-ray photography is carried out.

Hereupon, there are cases where the patient is exited and causes cardiac convulsion for longer than 15 to 30 sec during the inspection. In the case where the cardiac convulsion continues for a long time, the stagnation of the blood occurs, thereby causing the damage of the cerebral cells, etc. Accordingly, a high voltage shock of 3000 to 5000 V is given to the heart of the patient while using a defibrillator ordinarily.

The conventional defibrillator has a shape of a box provided with a handle on the upper part thereof, and the electric shock is given by pressing the electrode part which is disposed on the lower surface of the box on the region of the heart of the patient.

However, in the case of using the conventional defibrillator, it is necessary to use the defibrillator after taking out it on each time when the cardiac convulsion is caused on the patient.

Namely, it is very much troublesome to use the conventional defibrillator and particularly, there is a fear of too late to meet an emergent requirement.

Moreover, there are cases where an electrode has been preliminarily adhered onto the surface of the body of the patient due to the necessity of taking electrocardiogram during X-ray photographing. However, since the conventional electrode is made of a metal and does not transmit X-ray, such an electrode has been an obstacle to the X-ray photography.

As a result of the present inventors' studies for solving the above-mentioned problems, it has been found that the whole electrode can be made to be transparent to X-ray by making the electrode substrate of the porous material mainly consisting of granular or fibrous carbon or of the flexible and porous material mainly consisting of fibrous carbon, and on the basis of the above-mentioned finding, the present inventors have attained the present invention.

Namely, the object of the present invention is to provide an electrode for a living body which has been constituted so that the whole electrode is transparent to X-ray and does not hinder the X-ray inspection by making the electrode substrate of the porous material composed of granular or fibrous carbon, or of the flexible and porous material composed of fibrous carbon.

SUMMARY OF THE INVENTION

In a first aspect of the present invention, there is provided an electrode for a living body, wherein the electrode is provided with the electrode substrate comprising a porous material composed of granular or fibrous carbon and is substantially transparent to X-ray, the pores in the electrode substrate being impregnated with an electrolyte solution In a second aspect of the present invention, there is provided an electrode for a living body, wherein the electrode is provided with the electrode substrate comprising a flexible and porous material composed of fibrous carbon and is substantially transparent to X-ray, the pores in the electrode substrate being impregnated with an electrolyte solution.

BRIEF EXPLANATION OF DRAWINGS

Of the attached drawings,

FIG. 1A and FIG. 1B show the vertical section of the electrode of a defibrillator according to the example of the present invention, and more in detail, FIG. 1A shows the electrode provided with an electrode substrate comprising the porous material composed of granular or fibrous carbon, and FIG. 1B shows the electrode provided with an electrode substrate comprising the flexible and porous material composed of fibrous carbon.

DETAILED DESCRIPTION OF THE INVENTION

In the following, the examples wherein the present invention is applied to the electrode of a defibrillator will be explained while referring to the attached drawings.

Figure 2A:
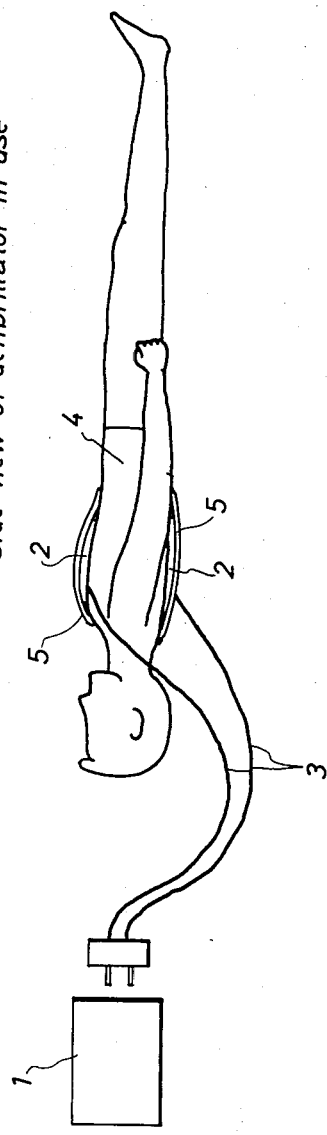
FIG. 2A and FIG. 2B are respectively the side view of and the plane figure of a main part of the electrode substrate of the defibrillator in use.
Figure 2B:
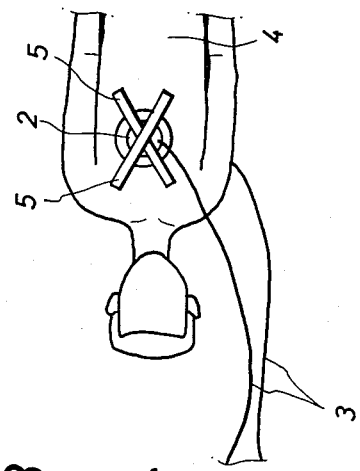

As has been shown in FIGS. 2A and 2B, the defibrillator consists of the high pressure-generating part 1, a pair of electrodes 2 and the lead part 3 which connects the above-mentioned parts, and each of the electrodes 2 is installed on the heart region of the patient 4 from the breast side and the back side.

As has been shown in FIGS. 1A and 1B, each electrode is directly adhered to the skin of the patient 4 via a suitable adhesive and is further fixed by a band 5. It is necessary that the electrode of the defibrillator is fixed firmly in particular, because the electrode is apt to come off from the living body by the shock of high voltage.

As has been shown in FIGS. 1A, 1B, 3A and 3B, each of the electrode substrate 20 consists of a disk-like porous carbonaceous material of about 50 cm$^2$ in area and 0.1 to 1 mm in thickness (hereinafter such an electrode substrate is referred to as the porous electrode substrate) or of a disklike flexible and porous carbonaceous material of about 50 cm$^2$ in area and about 0.1 to 2 mm in thickness (hereinafter such an electrode substrate is referred to as the flexible electrode substrate). In addition, 7 in FIGS. 1A and 1B is a ring-form sponge for covering and 8 is a protective membrane provided on the upper surface of the electrode substrate 20.

Figure 3A:
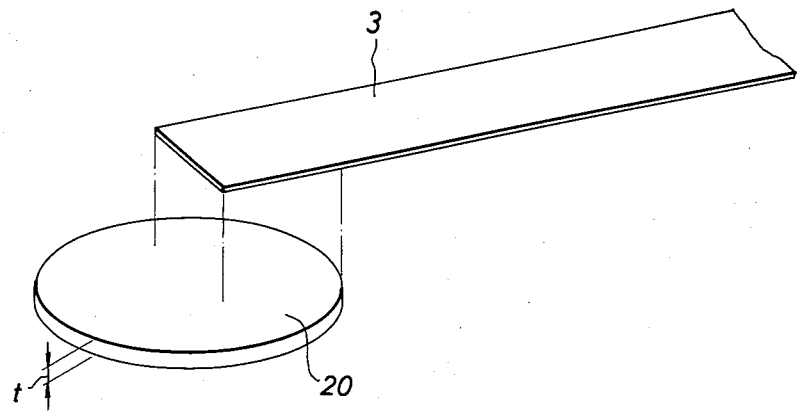
FIG. 3A is an analytical oblique view showing the junction of the electrode and the lead part according to one of the examples of the present invention.
Figure 3B:
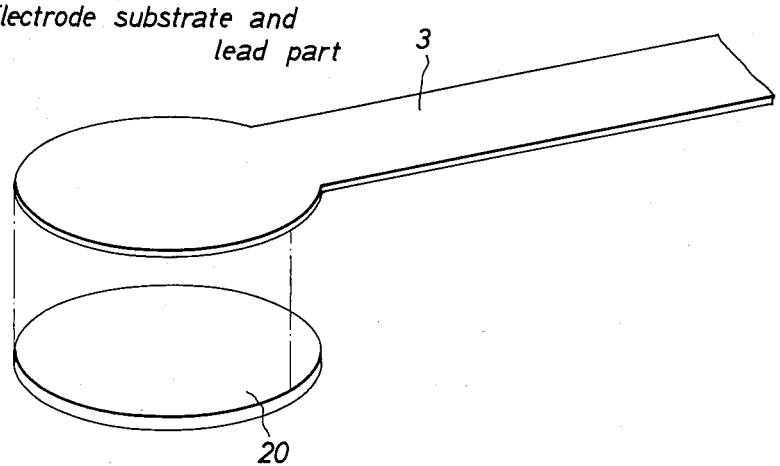
FIG. 3B is an analytical oblique view showing the junction of the electrode and the lead part according to another example of the present invention.

As has been shown in FIGS. 3A and 3B, the thickness (t) of the electrode substrate 20 is preferably not more than 10 mm and more preferably not more than 2 mm. In the case where the thickness (t) is more than 10 mm, it is not favorable, because such an electrode substrate gives an unfamiliar feeling to the living body.

Furthermore, particularly in the case of the defibrillator, since a large current is applied under a high voltage of 3000 to 5000 V, the electrical resistance of the electrode substrate 20 is preferably not more than 1.0Ω. In the case where the resistance is too high, there is fear of burns due to the generation of heat in the electrode.

The porous electrode substrate 20 comprises a sheet-like porous material produced by (1) manufacturing an original sheet-like material from relatively long carbon fibers of not less than 3 mm in length by a paper-manufacturing method, (2) impregnating the thus manufactured original sheet-like material with a thermosetting resin such as phenol resin, epoxy resin, etc., thereby binding the carbon fibers to each other and (3) carbonizing the thus impregnated material by calcining thereof under a reduced pressure or in an inert gas atmosphere. In addition, in the porous electrode substrate 20, a number of pores of a diameter of about 80 to 120 μm have been formed and the pores have been impregnated with a jelly-like electrolyte solution such as a physiological saline solution, etc.

Furthermore, the porous electrode substrate 20 may be constituted of a carbonaceous mold substrate plate scarcely showing flexibility.

Such a mold substrate plate can be obtained by (1) mixing fibrous carbon of not more than 3 mm in length or granular carbon of not more than 1 mm in diameter with particles of a thermosetting resin such as phenol resin, epoxy resin, etc., (2) molding the thus prepared mixture, for instance, at a temperature of 140° to 150° C. under a pressure of 50 kg/cm² G and then (3) calcining and carbonizing the thus molded material under a reduced pressure or in an inert gas atmosphere at a temperature of not less than 1500° C.

The thus obtained mold substrate plate nearly uniformly contains the pores of 20 to 80 μm in diameter at the porosity of 40 to 90%. Accordingly, in the case where these pores are impregnated with the electrolyte solution such as physiological saline solution, etc., the contact surface area between the pore and the electrolyte solution becomes 2 times as large as that in the above-mentioned example of the porous sheet-like material.

The flexible electrode substrate 20 has been composed of a flexible and porous carbonaceous material produced by (1) preliminarily subjecting relatively long carbon fibers of not less than 1 mm in length to heat treatment at a temperature of not less than 1500° C., more preferably not less than 2000° C., (2) manufacturing the thus treated carbon fibers into an original paper sheet-like material by a paper-manufacturing method, (3) impregnating the thus obtained paper sheet-like material with a thermosetting resin such as phenol resin, epoxy resin, etc. as a binding agent, thereby binding the carbon filaments to each other and then (4) calcining and carbonizing the thus impregnated material under a reduced pressure or in an inert gas atmosphere. In the thus produced flexible electrode substrate 20, a number of the pores of 20 to 120 μm in diameter are formed nearly uniformly at the porosity of 40 to 90%, and the pores have been impregnated with a jelly-like electrolyte solution such as physiological saline solution.

Before manufacturing the paper sheet-like material used for producing the flexible electrode substrate from the carbon fibers, it is necessary to previously subject the carbon filaments to high temperature treatment for inactivating the surface of the carbon fibers. The reason is as follows:

Within the flexible electrode substrate 20 after being carbonized, a number of mutually intersecting carbon fibers are restrained on each of the intersecting points by the carbon lumps derived from the binding agent. In such a situation, when the surface of the carbon fibers is made to be inactive, the carbon fibers and the carbon lump derived from the binding agent freely slide to each other and accordingly, a moderate flexibility is given to the electrode substrate on the whole.

In addition, in the case where the carbon fibers sheafed by using a sheafing agent are used, the sheafing agent on the carbon fibers is removed by washing with a solvent such as acetone, etc. and the thus washed carbon fibers are subjected to heat-treatment at a high temperature to inactivate the surface of the carbon fibers.

Figure 5:
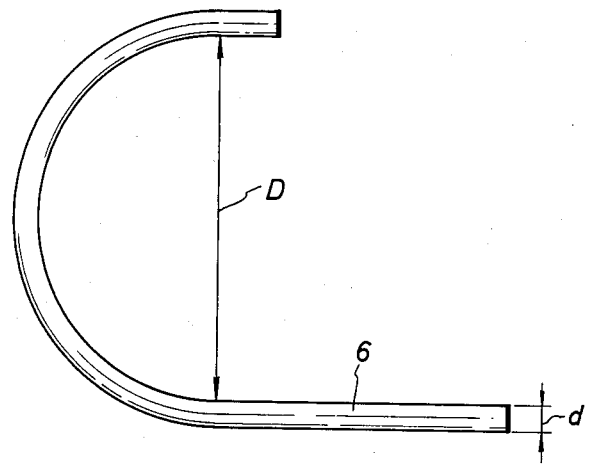

The flexibility of the flexible electrode substrate 20 is preferably so that, as is shown in FIG. 5, the flexible and porous carbon material 6 constituting the electrode substrate is not more than 200 in the value of the ratio (D/d), wherein D is the diameter of the curvature just before the breakage of the material 6 when it is bent until the breakage (the minimum diameter of the curvature) and d is the thickness of the material 6. In the case where the ratio (D/d) is over 200, the necessary flexibility is not available and since the following-up property and the close adhesiveness to the living body are reduced, the electrode becomes apt to come off from the living body by the high voltage shock, etc.

In order to improve the affinity of the electrode substrate to the living body and in the same time, in order to improve the adhesiveness of the electrode substrate to the living body and to improve the buffering property thereof to the high voltage shock, a buffering material 21 such as a sponge impregnated with a physiological saline solution, etc. is usually provided between the porous electrode substrate 20 and the living body as seen from FIG. 1A, and is preferably provided between the flexible electrode substrate 20 and the living body as seen from FIG. 1B.

In addition, the lead part 3 of the defibrillator is preferably composed of a flexible graphite sheet while particularly being located in the vicinity of the electrode 2.

Such a flexible graphite sheet may be produced by high pressure molding of the expanded graphite particles obtained by treating graphite particles with 98% concentrated sulfuric acid, for instance, it may be GRAFOIL ® (made by Union Carbide Corporation).

An example of the lead part 3 composed of GRAFOIL ® is shown in FIG. 3A.

Since GRAFOIL ® may be molded into an optional form by cold punching method, it is excellent in mass production and in the same time, the contact resistance between the lead part 3 and the electrode substrate 20 can be reduced to the negligible extent.

The adhesion of the electrode substrate 20 to the lead part 3 can be carried out by the use of an electroconductive adhesive prepared by admixing micro-particles of carbon such as carbon black with a thermosetting resin. As the thermosetting resin for use in the object, phenol resin, epoxy resin, etc. may be mentioned. The amount of microparticles of carbon admixed is preferably 30 to 90% by weight of the mixture.

In the case where the amount of micro-particles of carbon admixed is below 30% by weight, the necessary electroconductivity cannot be obtained, and on the other hand, in the case where the amount of micro-particles of carbon admixed is over 90% by weight, the adhesive strength becomes too small.

As the electroconductive adhesive, a mixture prepared by admixing micro-particles of carbon such as carbon black with a rubber-like resin may be used. The rubber-like resin which is usable for the object may be either the natural crude rubber or the synthetic crude rubber. Furthermore, the amount of micro-particles of carbon admixed is preferably 30 to 90% by weight of the mixture by the same reason as above. According to the above-mentioned method, although the adhesive strength is relatively small, it is able to provide the joining part with a flexibility.

Furtheremore, as another method of joining the electrode substrate 20 to the lead part 3, the following method may be mentioned. Namely, at first, the electrode substrate 20 and the lead part 3 are joined together by using an adhesive prepared by admixing micro-particles of carbon such as carbon black with a thermosetting resin, and then the thus joined part is calcined and carbonized under a reduced pressure or in an inert gas atmosphere at a temperature of not less than 1000° C. According to the above-mentioned method, the electric resistance of the joined part can be reduced to the negligible extent. As the thermosetting resin for use in the above-mentioned method, phenol resin, epoxy resin, etc. may be mentioned. The amount of micro-particles of carbon admixed is preferably not more than 90 % by weight of the mixture. In the case where the amount of micro-particles of carbon admixed is too large, there is a fear of reducing the adhesive strength.

According to the above-mentioned construction, the electrode 2 including the lead part 3 is substantially transparent to X-ray. Consequently, the electrode does not hinder X-ray photography, and the electrode can be installed always on the living body during X-ray inspection.

In addition, as the lead part 3, carbon fibers may be used, however, in such a case, the junction of the lead part and the electrode substrate is relatively difficult accompanying the demerits due to the increased electric resistance and the great bulk of the lead part. The above-mentioned lead part 3 composed of GRA-FOIL ® solves all the just mentioned problem.

FIG. 3B shows an example in which the adhesion or the calcining junction of the lead part 3 and the electrode substrate 20 is carried out all over the opposite surface of the electrode substrate 20 to the surface thereof which contacts to the living body. Namely, the above-mentioned example in FIG. 3B is an example in which the shape of the joining surface of the lead part 3 is the same as the shape of the surface of the electrode substrate 20. In such a construction, the joining area is large so that the adhesive strength is large and the contact resistance is small.

Figure 4:
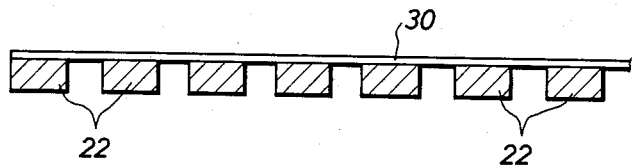
FIG. 4 shows the vertical section of the electrode according to another example of the present invention and FIG. 5 is an oblique view showing the flexibility of the flexible sheet.

FIG. 4 shows another example of the present invention. In the example shown in FIG. 4, the electrode is so constructed that a plurality of the electrode substrate blocks 22 are adhered to the flexible graphite sheet 30. By dividing the electrode substrate into a plurality of blocks, the surface of the electrode which faces to the living body has a freely bendable structure. In addition, the block 22 of the porous electrode substrate may be made of the same material as that of the above-mentioned electrode. Furthermore, the flexible graphite sheet 30 may also serve the lead part.

Although the examples wherein the present invention has been applied to the defibrillator were explained as above, the present invention can be applied to the electrode for electrocardiograph, and the electrode according to the present invention can be used as the electrode both in the defibrillator and the electrocardiograph. In addition, the present invention can be applied to the X-ray transmitting-type electrode for a living body which is used for measuring electroencephalogram, etc.

Since in the present invention, the electrode substrate has been mainly composed of granular or fibrous carbon, thereby making the whole electrode substantially transparent to X-ray, such an electrode does not hinder the X-ray photographing even in the case where the electrode is always installed on the living body. Accordingly, the electrode according to the present invention can be used as the electrode for an electrocardiograph or a defibrillator of always-installed type during X-ray inspection.

In addition, in the case where the porous and flexible carbon sheet is used as the surface of the electrode which contacts directly to the living body, the contact surface of the electrode is freely bendable. Accordingly, the close adhesion of the electrode to the living body is excellent, and the electrode does not come off by shocks, etc. even in the case where the electrode according to the present invention is used as the electrode of the defibrillator.

What is claimed is:

1. An X-ray transparent electrode for contacting a living body provided with (1) an electrode substrate comprising a porous material composed of granular or fibrous carbon, the electrode substrate having a surface adapted to contact a living body and (2) a lead part comprising a flexible graphite sheet, said lead part joined to said electrode substrate by an electroconductive adhesive prepared by a mixture of carbon microparticles and a thermosetting resin which has been calcined and carbonized under a reduced pressure or an inert gas atmosphere at a temperature of not less than 1000° C., the electrode being substantially transparent to X-ray, and the pores in said electrode substrate being impregnated with an electrolyte solution.

2. An X-ray transparent electrode for a living body according to claim 1, wherein the calcined junction of said lead part and said electrode substrate is over the entire surface of said electrode substrate opposite to the surface thereof which contacts the living body.

3. An X-ray transparent electrode for a living body according to claim 1, wherein said thermosetting resin is a phenol resin or an epoxy resin.

4. An X-ray transparent electrode for a living body according to claim 1, wherein said microparticles of carbon are carbon black.

5. An X-ray transparent electrode for a living body according to claim 1, wherein a sponge-like, porous buffering material impregnated with an electrolyte solution is provided on the body-contacting surface of said electrode substrate.

6. An X-ray transparent electrode for a living body according to claim 1, wherein said electrode substrate comprises a calcined, porous, sheet-like material comprising carbon fibers not less than 3 mm in length with a thermosetting resin and calcined under reduced pressure or in an inert gas atmosphere.

7. An X-ray transparent electrode for a living body according to claim 6, wherein the porous, sheet-like material has a plurality of pores having a diameter of about 80 to 120 μm therein in which the pores are impregnated with said electrolyte solution.

8. An X-ray transparent electrode for a living body according to claim 6, wherein said thermosetting resin is a phenol resin or an epoxy resin.

9. An X-ray transparent electrode for a living body according to claim 1, wherein said electrode substrate comprises a porous, molded substrate plate composed of a calcined, thermally molded mixture of carbon fibers of not more than 3 mm in length, or granular carbon of not more than 1 mm in diameter, and particles of a thermosetting resin, the molded material calcined under reduced pressure or in an inert gas atmosphere.

10. An X-ray transparent electrode for a living body according to claim 9, wherein said electrode substrate contains pores of 20 to 80 μm in diameter at the porosity of 40-90% of uniformity, said pores being impregnated with said electrolyte solution.

11. An X-ray transparent electrode for a living body according to claim 9, wherein said thermosetting resin is a phenol resin or an epoxy resin.

* * * * *